(12) United States Patent
Park et al.

(10) Patent No.: US 7,079,896 B1
(45) Date of Patent: Jul. 18, 2006

(54) METHODS OF AUTOMATICALLY OPTIMIZING AV DELAY BY WAY OF MONITORING THE HEART SOUND

(75) Inventors: Euljoon Park, Valencia, CA (US); Taraneh Ghaffari Farazi, San Jose, CA (US)

(73) Assignee: Pacesetter, Inc., Sylmar, CA (US)

( * ) Notice: Subject to any disclaimer, the term of this patent is extended or adjusted under 35 U.S.C. 154(b) by 608 days.

(21) Appl. No.: 10/302,652

(22) Filed: Nov. 22, 2002

Related U.S. Application Data

(60) Provisional application No. 60/333,914, filed on Nov. 26, 2001.

(51) Int. Cl.
*A61N 1/365* (2006.01)

(52) U.S. Cl. ........................................ 607/17; 600/528

(58) Field of Classification Search ................ 600/528, 600/586; 607/9, 17–19, 24
See application file for complete search history.

(56) References Cited

U.S. PATENT DOCUMENTS

| 5,554,177 A | 9/1996 | Kieval et al. ................ 607/17 |
| 5,609,612 A * | 3/1997 | Plicchi et al. ................ 607/17 |
| 5,700,283 A | 12/1997 | Salo ............................ 607/17 |
| 5,935,081 A | 8/1999 | Kadhiresan ................ 600/513 |
| 5,991,661 A | 11/1999 | Park et al. .................... 607/19 |
| 6,044,298 A | 3/2000 | Salo et al. .................... 607/17 |
| 6,058,329 A | 5/2000 | Salo et al. .................... 607/17 |
| 6,409,675 B1 | 6/2002 | Turcott ....................... 600/508 |
| 6,477,406 B1 | 11/2002 | Turcott ....................... 600/518 |
| 6,480,733 B1 | 11/2002 | Turcott ....................... 600/516 |
| 6,792,308 B1 * | 9/2004 | Corbucci ..................... 607/17 |
| 2002/0151938 A1 | 10/2002 | Corbucci ..................... 607/25 |
| 2004/0024423 A1 | 2/2004 | Lincoln et al. ............... 607/17 |

* cited by examiner

Primary Examiner—Robert E. Pezzuto
Assistant Examiner—Kristen Mullen

(57) ABSTRACT

An implantable cardiac stimulator including and accelerometer utilizes heart sound measurements to optimize the AV delay. One or more of the amplitude of the heart sound, the pre-ejection interval or the ejection interval is derived from the measurements and examined at various values of AV delay. The optimal AV delay is selected that corresponds to the highest cardiac function such as contractility, cardiac output and stroke volume. The stimulation device determines when the patient is at rest and the accelerometer provides a signal that corresponds to the audible component of a vibration produced as a result of ventricular contraction, blood movement toward the atrium, and the opening and closing of valves. The AV delay is adjusted within a range of values and the cardiac parameters are determined multiple times for each AV delay value. The average value of the cardiac parameter is examined to determine the optimal AV delay value.

23 Claims, 4 Drawing Sheets

FIG. 3
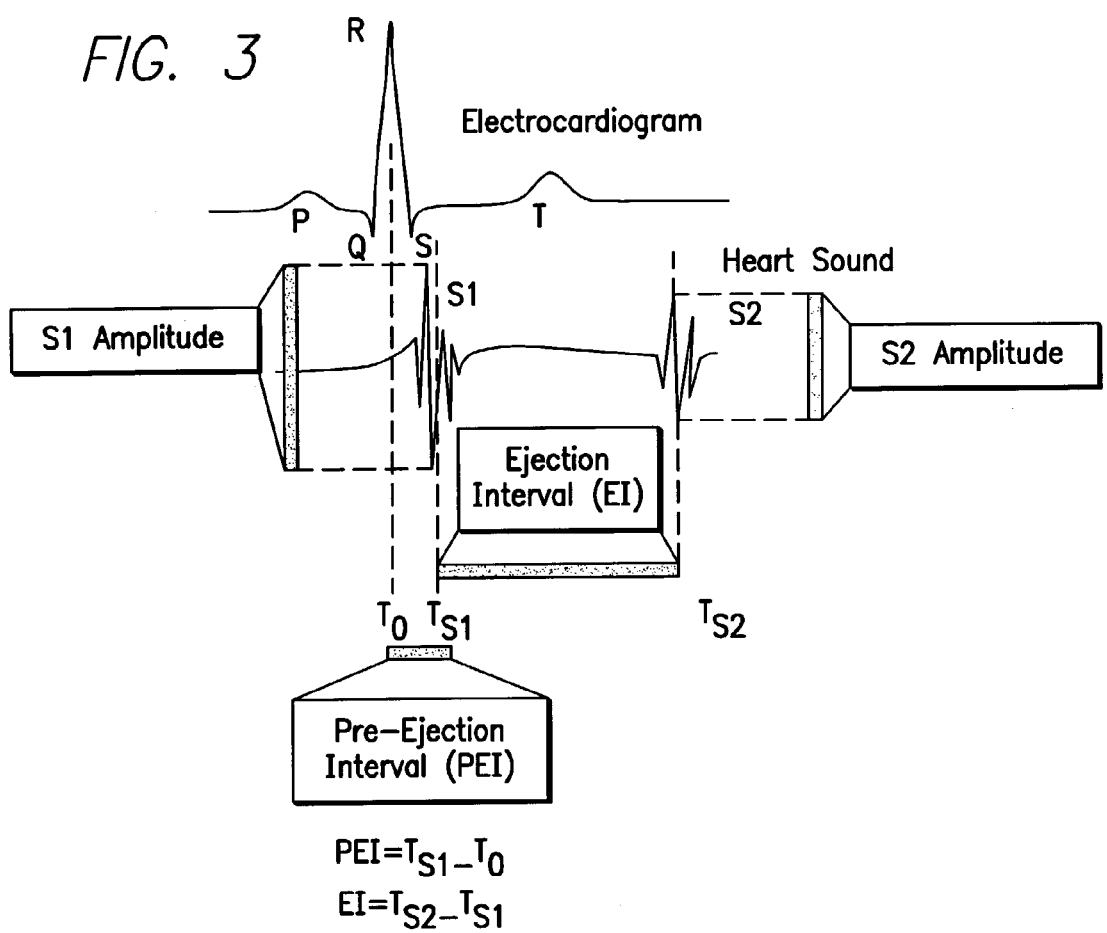
$PEI = T_{S1} - T_0$
$EI = T_{S2} - T_{S1}$
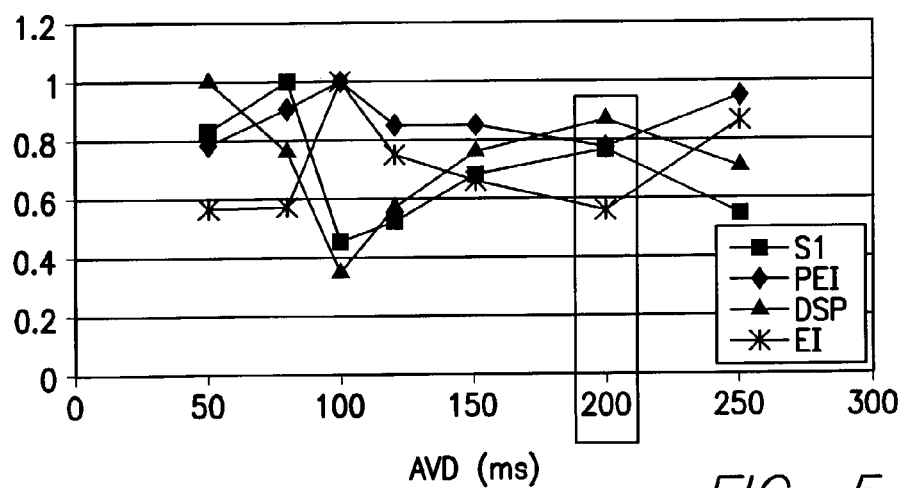
FIG. 5

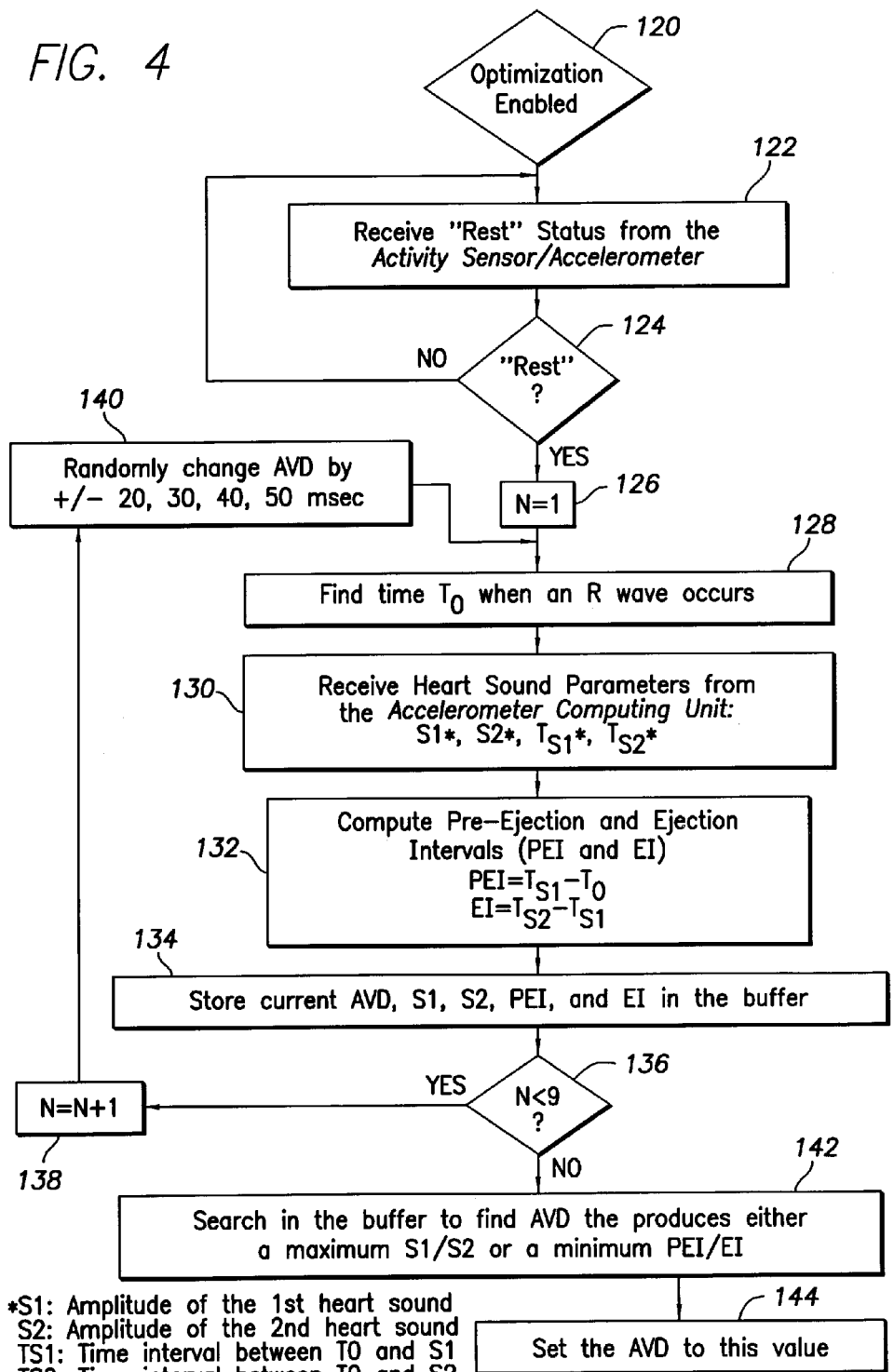

METHODS OF AUTOMATICALLY OPTIMIZING AV DELAY BY WAY OF MONITORING THE HEART SOUND

CROSS REFERENCE TO RELATED APPLICATIONS

This application claims the benefit of U.S. Provisional Patent Application Ser. No. 60/333,914, filed Nov. 26, 2001.

BACKGROUND OF THE INVENTION

1. Field of the Invention

The present invention is directed to a method for automatically optimizing AV delay adjusted in an implantable cardiac stimulation device by using and analyzing parameters derived from heart sound.

2. Background

Implantable medical devices such as cardiac pacemakers and cardioverter defibrillators are configured to monitor the electrical activity in various chambers of a patient's heart. In doing so, the devices can adjust selected operational parameters to maintain desired cardiac function. One such cardiac function is cardiac output and one such operational parameter is atrioventricular delay (hereinafter "AV delay"). The proper setting of the AV delay can be crucial in establishing and maintaining the desired cardiac function, which contributes markedly to the patient's quality of life. It is recognized that improper setting of such device parameters, not only has a negative effect on the patient's quality of life, but may create permanent functional impairment of the patient's heart over time. Moreover, manual optimization of operational parameters such as AV delay, which may be undertaken at implant or at follow-up, may not prove to be optimum at some later date due to changes in the patient's health status, activity level, medication intake, disease progression as well as other factors impacting cardiac function.

The aim of pacing therapies in heart failure patients is the optimization of cardiac function. Implantable pacemakers are increasingly used in patients with congestive heart failure because they have proven to be very effective in enhancing cardiac function. Mechanisms that contribute to such functional improvement include an increase in filling time, improved cardiac contractility, improved right ventricular and left ventricular systolic and diastolic function, greater cardiac output and a decrease in mitrial regurgitation. However, unless stimulation devices are optimized for each individual patient, it is unlikely that appropriate and efficient pumping action and therefore cardiac output will be achieved. In that regard, it is recognized that adjusting the AV delay will either directly or indirectly affect one or more of the above identified mechanisms. Accordingly, optimization of the AV delay achieved automatically by continuous measurement and monitoring of several parameters, in particular those related to heart sound, can further improve cardiac function. Heretofore, abnormal heart sounds have been detected by the use of an acoustic sensor located in proximity to a patient's heart as is described in U.S. Pat. No. 5,554,177 to Kieval et al. The characteristics of the heart sounds, detected by the acoustic sensor, are detected during adjustments in the timing sequence of pacing pulses and pacing therapy is adjusted to achieve an improved heart function. The method described requires the use of a separate acoustic sensor(s) or microphones which not only compounds the complexity of the system, but markedly adds to its cost. Moreover the sensors as described in the '177 patent, are located outside of the stimulation device and placed at various locations in the body such as the chest and sternum. Obviously, this requires significant additional surgery to implement the system with the attendant major increase in patient discomfort as well as the cost of implant. Accordingly what is needed is a reliable and minimum cost approach to implementing heart sound detection and processing to optimize AV delay settings for improving cardiac function, preferably utilizing an activity sensor typically included in rate responsive cardiac stimulation devices.

SUMMARY

A method is described for utilizing heart sound measurements monitored by means of an accelerometer based activity sensor to optimize AV delay and as a measure of the progression or regression of heart disease. The accelerometer included in the cardiac stimulation device, is responsive to chest vibration following as a consequence of heart contraction, which correlates with heart sound. In a normal cardiac cycle, there are two major sounds, identified as the first S1 and the second S2. S1 is the audible component of a vibration produced as a result of ventricular contraction, movement of blood towards the atrium, the opening of the aortic and pulmonary valves and the closing of the atrioventricular valves (mitral and tricuspid valves). S2 is the audible component of a vibration produced as a result of closing of the aortic and pulmonary valves. The maximum values of S1 and S2 are determined by their peak to peak values over a defined time interval.

These vibrations are transmitted through the heart and the chest and are detected by the device's accelerometer. The present invention undertakes optimizing AV delay by analyzing one or more parameters of heart sound. In addition to S1 and S2, such parameters include pre-ejection interval, ejection interval and cardiac wall displacement. A larger S1 and S2 amplitude, a larger displacement amplitude and shorter pre-ejection interval (PEI) and ejection interval (EI), all contribute to increased cardiac contractility. Monitoring one or more of these parameters provides the capability of monitoring cardiac contractility and thus the progression or regression of heart disease. Based upon inspection of these parameters, a number of different AV delays can be examined to determine the optimal AV delay that yields the highest cardiac output.

The process of optimizing AV delay is preferably undertaken when the patient is in a rest condition as determined, typically, by examining the accelerometer signal. If the accelerometer signal is below a specified threshold value, meaning that patient activity is at a minimum, then it is determined that the patient is at rest. The AV delay is randomly adjusted through a range of values and the values of the heart sound parameters S1, S2, displacement, PEI and EI are detected or calculated as the case may be, and stored in association with the AV delay giving rise to the value of each such heart sound parameter. The value of one or more of each heart sound parameter is examined to determine at which AV delay the cardiac output is at a maximum. The optimum AV delay is then set to that value associated with the maximal cardiac output. As an example, the AV delay is randomly adjusted to have eight different values and the value of S1 is detected and stored in association with each AV delay value. The eight S1 values are examined to determine its maximum value and the optimum AV delay is selected as that which produced such maximum value of S1. The AV delay is adjusted randomly to avoid any potential of "training" the heart in response to repetitive pacing at the same AV delay. In determining the optimum AV delay, examination is undertaken for S1, S2 and displacement being maximized and PEI and EI being minimized. Although results based upon the above procedure are expected to yield reliable values for the optimum AV delay, further reliability may be achieved by obtaining an average of a heart sound parameter value over a selected number of beats, typically eight, at the same adjusted AV delay value. Furthermore, although the optimum AV delay may be determined using one heart sound parameter, it is within the contemplation of the present invention to use a combination of more than one parameter to determine the optimum AV delay. It has been determined that there is a good correlation between the heart sound parameters and AV delay and either one or more heart sound parameters may be used in optimizing AV delay.

The PEI is calculated from the equation: $PEI=T_{S1}-T_0$, where $T_0$ is the time of occurrence of an R-wave and $T_{S1}$ is the time of occurrence of S1 sound calculated from the following equation:

Calculating $T_{S1}$ using the $2^{nd}$ moment:

$$T_{S1} = \frac{\sum_{t=T_0}^{T_0+RT} A_t^2 \cdot (t-T_0)}{\sum_{t=T_0}^{T_0+RT} A_t^2}$$

where $A_t$ is the instantaneous value of the accelerometer signal at time t and RT is the time of occurrence of a T-wave relative to the preceding the R-wave.

In a similar fashion the EI is calculated from the equation: $EI=T_{S2}-T_{S1}$, where $T_{S2}$ is the time of occurrence of S2 sound. Using the second moment, $T_{S2}$ is calculated from the following equation:

$$T_{S2} = RT + \frac{\sum_{t=RT}^{nextT_0} A_t^2 \cdot (t-RT)}{\sum_{t=RT}^{nextT_0} A_t^2}$$

where next $T_0$ represents the occurrence of an R-wave immediately following the T-wave.

The second moment is preferred over the first moment where the acceleration value $A_t$ is used directly rather than the square of the value, because the second moment is immune to noise much more so than the first moment.

Advantageously, the heart sound parameters and AV delay may be stored in memory periodically, perhaps daily or weekly or other time frames at the choice of a physician, for up to six to twelve months. Parameters recorded on different dates can be displayed at the time of interrogation and their comparison can give clues in determining whether the heart disease has progressed or not. This information can also be used to modify therapy, which includes V—V timing in multi chamber pacing to improve cardiac trends.

BRIEF DESCRIPTION OF THE DRAWINGS

Further features and advantages of the present invention may be more readily understood by reference to the following description taken in conjunction with the accompanying drawings, in which:

FIG. 3 is a depiction of a QRS complex and the identification of the resulting heart sound parameters;

FIG. 4 is a flow chart describing an overview of the operation of an embodiment of the present invention; and FIG. 5 is a graph of normalized heart sound parameters versus AV delay for a patient.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
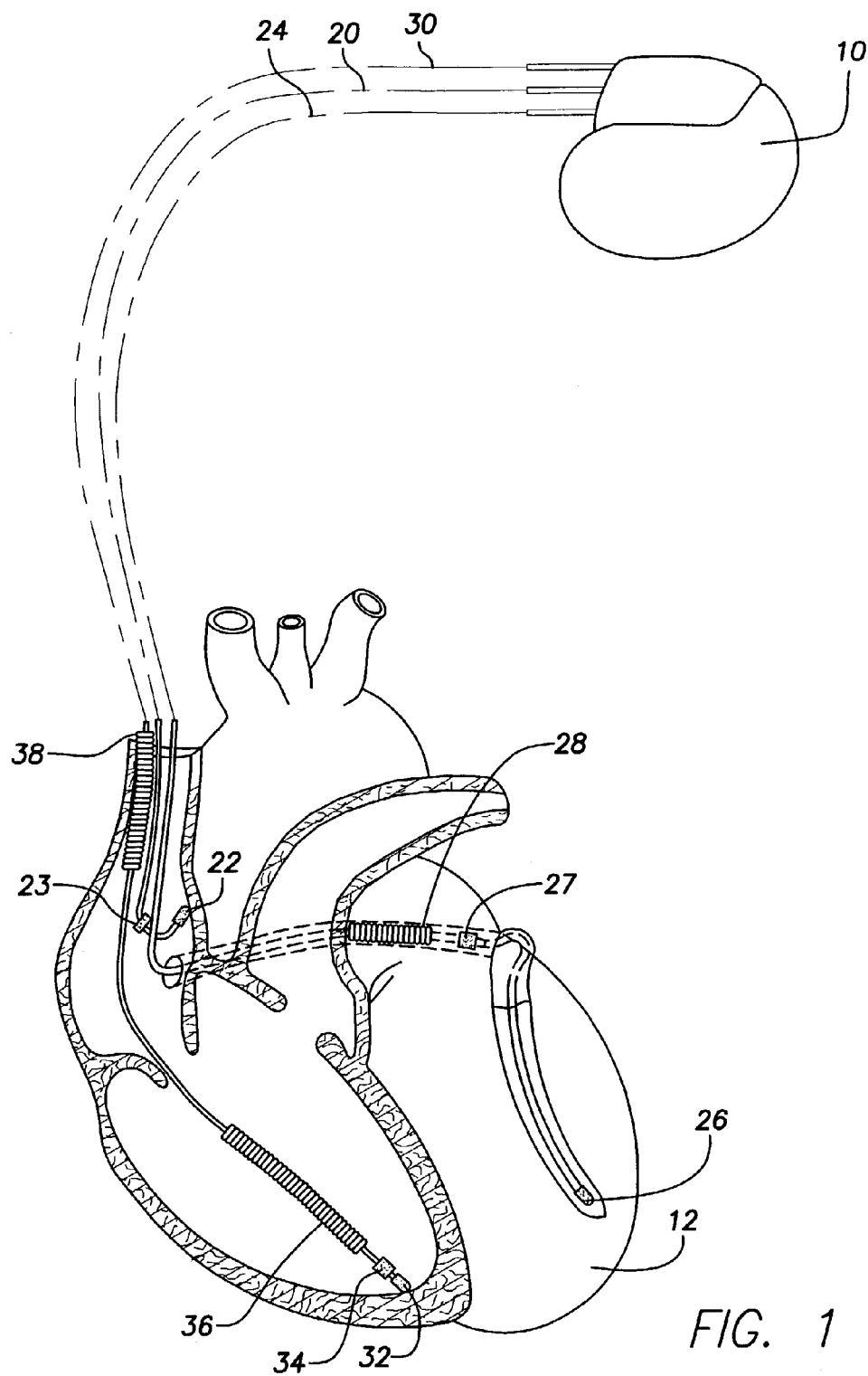
FIG. 1 is a simplified diagram illustrating an implantable stimulation device in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
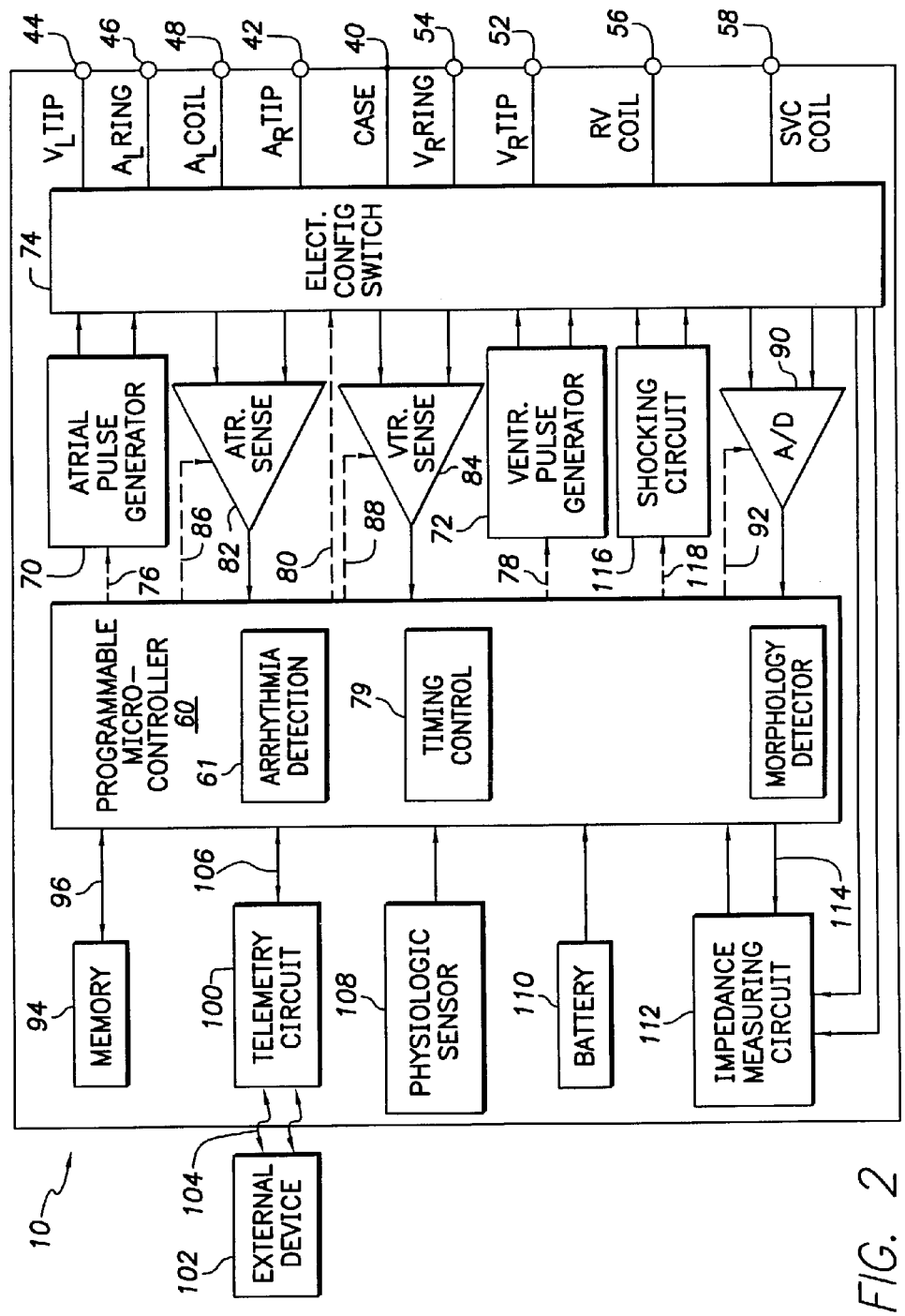
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60, which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals. Sensed events include P-waves, R-waves, and depolarization signals associated with fibrillation, which are sometimes referred to as "F-waves" or "Fib-waves".

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. A feature of the present invention is the ability to sense and store a relatively large amount of data (e.g., from the data acquisition system 90), which data may then be used for subsequent analysis to guide the programming of the device and for the adjustment of programmable parameters such as AV Delay.

The operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 allows intracardiac electrograms and status information relating to the operation of the device 10 (as contained in the microcontroller 60 or memory 94) to be sent to the external device 102 through an established communication link 104.

In the a first embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

The present invention utilizes an accelerometer that provides a measure of the physical motion of the patient as well providing a sensor to be used as a measure of the instantaneous pumping function of the heart such as for example, cardiac output, contractility and stroke volume. It is recognized that the contractility of the heart, which is influenced by the value of the AV delay, may be determined in a variety of ways, For a discussion of the use of an accelerometer based activity sensor to obtain parameters that are indicative of the heartbeat of a patient see U.S. Pat. No. 5,991,661 to Park, et al. which patent is incorporated herein by reference.

However, for convenience and simplicity, it is preferred to employ a technique that does not require a special lead, for example, by measuring the heart sounds. As will be described below, heart sounds may be obtained by thoracic movement due to heart contractions using an accelerometer in the device. Other methods of measuring heart sound include the use of an acoustic sensor as described in U.S. Pat. No. 5,554,177 to Kieval et al.

In another embodiment, the data acquisition system 90 may acquire the intracardiac electrogram through the pacing/sensing electrodes (e.g., ventricular electrodes 32, 34 and/or atrial electrode 22, 24) or by a sensor in the housing itself, so that the signal conditioning circuit 120 can determine the patient's current contractility based on, such as for example, heart sounds. Heart sound waves can be used to determine contractility and other related parameters (e.g., stroke volume, blood pressure and dP/dt), as disclosed in U.S. Pat. No. 6,044,299 (Nilsson), which is hereby incorporated herein by reference.

An aspect of the present invention as described below is a method of using heart sound measurements to optimize AV delay and to monitor the progression or regression of heart disease. This may be accomplished by the use of signals that represent a measure of heart sound. In a normal cardiac cycle, there are two major sounds that may be referred to as the first sound S1 and the second sound S2 as are shown in the electrocardiogram (ECG) of FIG. 3. The heart sound S1 is the audible component of a vibration produced in the heart as a result of ventricular contraction, movement of blood toward the atrium, the opening of aortic and pulmonary valves and the closing of the mitrial and tricuspid valves (atrioventricular valves). The heart sound S2 is the audible component of a vibration produced as a result of the closing of the aortic and pulmonary valves. Since these vibrations are transmitted through the heart and the chest, the vibrations may be detected by a motion sensor, such as physiologic sensor 108, included within the stimulation device 10. For the present invention, an accelerometer is used as an activity or physiologic sensor 108 to detect, in addition to patient activity, the transmitted cardiac vibrations. The signal provided by the accelerometer, especially when the patient is at rest, may be used as a measure of heart sound.

With reference to FIG. 3, a QRS complex, as may be detected by right ventricular lead 30, is shown with $T_0$ positioned at the time of occurrence of the R wave or a paced ventricular pulse V. In the present context, reference to an R wave includes a paced ventricular pulse (stimulation pulse) because optimization of AV delay relies on optimizing the timing of a ventricular stimulation pulse in order to obtain improved pumping function and therefore improved cardiac output. As is recognized, changing the AV delay is accomplished by changing the timing of the delivery of the ventricular stimulation pulse. For purposes of this discussion, an R wave resulting from the delivery of a ventricular stimulation pulse may be referred to as a "paced R wave". Also shown in FIG. 3, is a P-wave representing the portion of the ECG representing atrial depolarization and a T-wave representing a ventricular repolarization. The S1 amplitude is determined, typically by the microcontroller 60, as the maximum peak to peak value of the accelerometer signal over a pre-defined interval which is roughly equal to the time between the occurrence of the R-wave and T-wave or otherwise known as the RT interval. The pre-defined interval may be pre-programmed in the stimulation device 10, programmed by the physician at implant or be continuously determined by stimulation device 10. The S2 amplitude is determined, typically by the microcontroller, as the maximum peak to peak value of the accelerometer signal over a pre-defined interval which is roughly equal to the time between the occurrence of the T-wave and next R-wave or otherwise known as the T-R interval. Similarly, the pre-defined interval (TR interval) may be pre-programmed in the stimulation device 10, programmed by the physician at implant or be continuously determined by stimulation device 10.

Also shown in FIG. 3 are the pre-ejection interval (PEI) calculated from the equation $PEI=T_{S1}-T_0$ and the ejection interval EI calculated from the equation $EI=T_{S2}-T_{S1}$. The value of $T_{S1}$ is calculated from either the first or second moment of the acceleration signal over the R-T interval and the value of $T_{S2}$ is calculated from either the first or second moment of the acceleration signal over the T-R interval. As will be described later, a larger S1, a larger displacement amplitude (second integral of the acceleration signal), and shorter PEI and EI intervals, all contribute to increased contractility as measured, by the present invention, by heart sounds. As was previously discussed, the value of the AV delay influences the contractility of the heart and therefore the heart sound. Thus, by varying the AV delay through a range of values, the optimum AV delay may be determined as that which leads to the highest contractility. That determination may be based on either the value of S1, displacement, PEI or EI or a combination of one or more of such parameters.

The value for $T_{S1}$ may be determined by the following equation:

Calculating $T_{S1}$ using the $1^{st}$ moment:

$$T_{S1} = \frac{\sum_{t=T_0}^{T_0+RT} A_t \cdot (t - T_0)}{\sum_{t=T_0}^{T_0+RT} A_t}$$

where $A_t$ is the instantaneous value of the accelerometer signal at time t.

As can be noted, the summation process commences at $t=T_0$ and continues to $t=T_0+RT$. The acceleration value may be the actual acceleration signal or a normalized value thereof, the necessary requirement being that the units remain consistent for all calculations. The incremental increase of time t or the $\Delta t$ from one acceleration measure to the next acceleration measure, is dependent in part, on the resolution of the accelerometer and a value of $\Delta t$, may for example, be in the range of about 1 to 10 milliseconds (ms). In a similar fashion the value of the first moment of $T_{S2}$ may be determined using the same equation immediately above with the value of $T_0$ set to the time of occurrence of the T-wave and the time t, taken from that point, to the occurrence of the next R-wave, that is, through the TR interval. However, to normalize the value of $T_{S2}$ relative to the value of $T_{S1}$, the value of the first moment calculation for $T_{S2}$ above, is increased by the value of the RT interval.

The value for $T_{S1}$ may also be determined by the following equation:

Calculating $T_{S1}$ using the $2^{nd}$ moment:

$$T_{S1} = \frac{\sum_{t=T_0}^{T_0+RT} A_t^2 \cdot (t - T_0)}{\sum_{t=T_0}^{T_0+RT} A_t^2}$$

As can be noted, the distinction between the $1^{st}$ and $2^{nd}$ moment calculation for $T_{S1}$, is that for the second moment, the value of the acceleration $A_t$ is squared. Although either the $1^{st}$ or $2^{nd}$ moment calculation is contemplated by the present invention, it is understood that the $2^{nd}$ moment calculation provides a more accurate timing calculation and is more immune to noise.

In a similar fashion the value of the second moment of $T_{S2}$ may be determined using the same equation immediately above with the value of $T_0$ set to the time of occurrence of the T-wave and the time t, taken from that point, to the occurrence of the next R-wave, that is, through the TR interval. However, to normalize the value of $T_{S2}$ relative to the value of $T_{S1}$, the value of the second moment calculation for $T_{S2}$ above, is increased by the value of the RT interval. The foregoing may be represented by the following equation:

$$T_{S2} = RT + \frac{\sum_{t=RT}^{nextT_0} A_t^2 \cdot (t - RT)}{\sum_{t=RT}^{nextT_0} A_t^2}$$

where next $T_0$ represents the occurrence of an R-wave immediately following the T-wave.

Although not shown, it is to be understood that the calculation of $T_{S2}$ using the first moment corresponds to the above equation using $A_t$ rather than that value squared. Subsequent to the calculation of $T_{S1}$ and $T_{S2}$, the pre-ejection interval PEI and the ejection interval EI are calculated from the following relationships:

$$PEI = T_{S1} - T_0 \text{ and } EI = T_{S2} - T_{S1}$$

Thus, with the determination of the parameters described above, the method of the present invention to optimize AV delay is undertaken under the control of microcontroller 60. To ensure minimum disturbance to the above calculations caused by patient activity, the optimization is undertaken when the patient is at rest.

With reference to FIG. 4, a flow chart of a method to optimize AV delay in accordance with an embodiment of the present invention is shown. At block 120, microcontroller 60 commands the initiation of the optimization procedure and in doing so monitors, in block 122, the output of the physiologic sensor 108 (hereinafter accelerometer 108). If the output of the accelerometer 108 indicates that the patient is in a rest condition, then a counter is set to the value "1" in block 126. Otherwise, the output of the accelerometer 108 is repeatedly rechecked until a rest condition is observed. A rest condition is observed when the output of the accelerometer 108 remains below a predefined low value for an extended pre-determined period of time. At block 128, the occurrence of an R-wave is time stamped as $T_0$, and in block 130 the values of S1 and S2 are determined by the microcontroller 60 and the values of $T_{S1}$ and $T_{S2}$ are calculated by the microcontroller 60, preferably using the $2^{nd}$ moment calculation method described above.

The pre-ejection interval PEI and the ejection interval EI are calculated from the following relationships: $PEI = T_{S1} - T_0$ and $EI = T_{S2} - T_{S1}$ in block 132 and the values of the current AV delay, S1, S2, PEI and EI are stored in a buffer (not shown) in microcontroller 60. A check is made in block 136 to determine whether the counter has exceeded a specific count, representing the number of iterations of the calculations and storage of the parameter values for S1, S2, $T_{S1}$, $T_{S2}$, PEI and EI for specific AV delay values. Although the total number of iterations is shown as eight (8) as a preferred number, it is within the contemplation of the present invention that such number may be increased or decreased depending upon the number of sample points desired. A higher number of samples with a decrease in the time interval between samples would provide a study with a higher resolution, if desired. If the count is less than 9, then the count is indexed by 1 in block 138 and the AV delay is randomly adjusted in block 140. Although the increments/decrements shown in block 140 are 50 ms or less, it is within the contemplation of the present invention that such time interval may be increased or decreased depending upon the range of AV delay values of interest and which are appropriate for a particular patient. With the value of AV delay adjusted, the values of S1, S2, $T_{S1}$, $T_{S2}$ PEI and EI are re-calculated and stored. As shown in block 140, the AV delay is changed randomly by adding and subtracting different time values to the current AV delay. Although adding and subtracting different time value may be undertaken in a stepwise progressive fashion, doing so randomly minimizes the potential of any bias in the calculation protocol.

When the count N reaches 9, the buffer in microcontroller 60 is searched through the range of calculated values to determine a local maximum for the parameters S1 and S2 and a local minimum for the parameters PEI and EI. Although selecting a parameter alone provides a reliable basis for determining the optimum AV delay, a more confident determination may be obtained with an inspection of all parameters or combinations thereof as the optimum AV delay selection criteria. The normalized results of an actual AV delay optimization study for a patient is shown in FIG. 5. As is observed, the initial AV delay was set at 50 ms and increased incrementally to 250 ms. For the study, cardiac displacement (DSP) was used rather than S2 as a recorded parameter. As further observed in FIG. 5 a local maximum for the parameters S1 and DSP and a local minimum for the parameters PEI and EI also occurred at 200 ms. On that basis a high degree of confidence is established that the optimal AV delay is 200 ms and in such cases the AV delay to the detected optimal value is accomplished in block 144. Although the value of S2 is not shown in FIG. 5, it is considered that S2 would also have a local maximum at 200 ms because the heart sound values are in good correlation. Furthermore, although it appears that a local maximum occurs between 50 ms and about 75 ms for displacement and S1, such values are not considered in selecting the optimum AV delay since such AV delay values are considered too short for normal cardiac operation and provide abnormal and premature cardiac contractions. In the process of selecting the optimum AV delay, the microprocessor 60 may be programmed to select only those AV delay values that are, for example, greater than 80 ms.

Physician attention to adjustment of the above described parameters is very important when considering device operation for improving the patient's quality of life. Typically, optimizing various ones of such patient dependent parameters is undertaken in a hospital or in a physician's office. Extreme care must be taken to avoid even slight inappropriate adjustment of device parameters which can cause functional impairment. Optimization of cardiac function by way of changing AV Delay has been shown to positively impact the enhancement of the heart's hemodynamic performance in both an efficient and expeditious manner while keeping the cost of the optimization at a minimum.

While the invention detailed above describes the use of heart sound to optimize AV delay, such should not be taken in a limiting sense and it is understood that those skilled in the art may apply the teachings herein to other applications without exceeding the scope and range of the invention as defined by he following claims.

What is claimed is:

1. In an implantable cardiac stimulation device for implant in a patient, said stimulation device having an accelerometer-based activity sensor and an adjustable AV delay, a method for optimizing said AV delay comprising:

determining when the patient is in a rest condition;

detecting the occurrence of R-waves when a rest condition is determined;

adjusting the AV delay through a range of values while monitoring an acceleration signal upon the occurrence of each R-wave;

storing the values of said acceleration signals in association with the corresponding values of the AV delay; and selecting the AV delay corresponding to the acceleration signal indicative of the highest cardiac contractility;

wherein monitoring an acceleration signal comprises detecting a maximum peak-to-peak accelerometer signal (S1) within a first pre-defined interval.

2. The method of claim 1 further comprising selecting the first pre-defined interval as the time from occurrence of an R-wave to occurrence of an immediately following T-wave.

3. The method of claim 1 wherein storing the value of said acceleration signal further comprises storing the acceleration value for a plurality of cardiac contractions at each AV delay value and determining an average value of the acceleration signal for the plurality of cardiac contractions at each AV delay value, and selecting the optimal AV delay corresponding to such average acceleration signal indicative of the highest cardiac contractility.

4. In an implantable cardiac stimulation device having an adjustable AV delay, a method for optimizing said AV delay comprising:

adjusting the AV delay through a range of values for said AV delay;

monitoring a heart sound parameter corresponding to cardiac contractility;

wherein the heart sound parameter is a cardiac pre-ejection interval and wherein the cardiac pre-ejection interval is a measure of cardiac contractility;

detecting a maximum value of said heart sound parameter indicative of cardiac contractility being maximized; and selecting the AV delay corresponding to the maximum value of said heart sound parameter;

wherein monitoring the pre-ejection interval (PEI) comprises calculating the PEI from the equation $PEI=T_{S1}-T_0$ where $T_0$ is the time of occurrence of an R-wave and $T_{S1}$ is calculated from the equation:

$$T_{S1} = \frac{\sum_{t=T_0}^{T_0+RT} A_t^2 \cdot (t-T_0)}{\sum_{t=T_0}^{T_0+RT} A_t^2}$$

where $A_t$ is the instantaneous value of the accelerometer signal at time t and RT is the time interval between the R-wave and the immediately following T-wave.

5. The method of claim 4, further comprising monitoring cardiac displacement as a measure of cardiac contractility.

6. The method of claim 5 wherein monitoring cardiac displacement comprises calculating a second integral of an accelerometer signal over a predetermined time interval.

7. The method of claim 4, further comprising monitoring cardiac ejection interval as a measure of cardiac contractility.

8. The method of claim 4 wherein monitoring the heart sound parameter comprises detecting a maximum peak-to-peak heart sound value within a first pre-defined interval.

9. The method of claim 5 further comprising selecting the first pre-defined interval as the time from the occurrence of an R-wave to the occurrence of an immediately following T-wave.

10. The method of claim 4 wherein monitoring heart sound comprises detecting a maximum peak-to-peak accelerometer signal (S2) within a second pre-defined interval wherein the second pre-defined interval is the time from the occurrence of a T-wave to the occurrence of an immediately following R-wave.

11. The method of claim 4 further comprising adjusting the AV delay when a patient is in a rest condition.

12. In an implantable cardiac stimulation device having an adjustable AV delay, a method for optimizing said AV delay comprising:
   adjusting the AV delay through a range of values for said AV delay;
   monitoring a heart sound parameter corresponding to cardiac contractility;
   wherein the heart sound parameter is a cardiac pre-ejection interval and wherein the cardiac pre-ejection interval is a measure of cardiac contractility;
   detecting a maximum value of said heart sound parameter indicative of cardiac contractility being maximized; and
   selecting the AV delay corresponding to the maximum value of said heart sound parameter;
   wherein monitoring the pre-ejection interval (PEI) comprises calculating the PEI from the equation $PEI=T_{S1}-T_0$ where $T_0$ is the time of occurrence of an R-wave and $T_{S1}$ is calculated from the equation:

$$T_{S1} = \frac{\sum_{t=T_0}^{T_0+RT} A_t \cdot (t-T_0)}{\sum_{t=T_0}^{T_0+RT} A_t}$$

where $A_t$ is the instantaneous value of the accelerometer signal at time t and RT is the time interval between the R-wave and the immediately following T-wave.

13. The method of claim 12 wherein monitoring the ejection interval (EI) comprises calculating the EI from the equation $EI=T_{S2}-T_{S1}$ where $T_{S2}$ is calculated from the equation:

$$T_{S2} = RT + \frac{\sum_{t=RT}^{nextT_0} A_t^2 \cdot (t-RT)}{\sum_{t=RT}^{nextT_0} A_t^2}$$

where $A_t$ is the instantaneous value of the accelerometer signal at time t and RT is the time interval between the R-wave and the immediately following T-wave and next $T_0$ is R-wave immediately following the T-wave.

14. An implantable cardiac stimulation device comprising:
   means for delivering stimulation pulses to a patient's heart;
   accelerometer sensing means for detecting one or more heart sounds as a measure of cardiac contractility and providing an accelerometer sensing means signal corresponding to the amplitude of the heart sound;
   wherein the measure of cardiac contractility comprises a cardiac pre-ejection interval (PEI);
   means for adjusting the AV delay through a range of values;
   means for storing the sensing means signal in association with the corresponding value of the AV delay; and
   means for selecting the AV delay corresponding to the maximum sensing means signal indicative of the maximum heart sound value;
   wherein the pre-ejection interval (PEI) comprises calculating the PEI from the equation $PEI=T_{S1}-T_0$ where $T_0$ is the time of occurrence of an R-wave and $T_{S1}$ is calculated from the equation:

$$T_{S1} = \frac{\sum_{t=T_0}^{T_0+RT} A_t^2 \cdot (t-T_0)}{\sum_{t=T_0}^{T_0+RT} A_t^2}$$

where $A_t$ the instantaneous value of the accelerometer signal at time t and RT is the time interval between the R-wave and the immediately following T-wave.

15. The implantable cardiac stimulation device of claim 14 further comprising means for determining when the patient is in a rest condition, and wherein the means for adjusting the AV delay is operative when the patient is determined to be in a rest condition.

16. The implantable cardiac stimulation device of claim 14 wherein the accelerometer sensing means further comprises means for detecting the maximum peak-to-peak sensing means signal (S1) within a first pre-defined interval.

17. The implantable cardiac stimulation device of claim 16 further comprising means for detecting the occurrence of an R-wave and means for selecting the first pre-defined interval as the time from the occurrence of an R-wave to the occurrence of an immediately following T-wave.

18. An implantable cardiac stimulation device comprising:
   a pulse generator adapted to deliver cardiac stimulation pulses to at least a ventricle of a patient's heart, the timing of delivery of such stimulation pulses being a function of an AV delay;
   an accelerometer, mounted within a housing, that senses heart sounds, the accelerometer being operative to provide accelerometer signals corresponding to sensed heart sounds;
   a control circuit coupled to the pulse generator and operative to adjust the AV delay through a plurality of AV delay values; and
   a monitoring circuit coupled to the accelerometer and operative to determine an optimal AV delay value based up the accelerometer signal corresponding to a maximum detected heart sound;
   wherein the monitoring circuit monitors cardiac pre-election interval as a measure of cardiac contractility;
   wherein the control circuit adjusts the AV delay to the optimal AV delay value; and wherein the pre-ejection interval (PEI) comprises calculating the PEI from the equation PEI=$T_{S1}$−$T_0$ where $T_0$ is the time of occurrence of an R-wave and $T_{S1}$ is calculated from the equation:

$$T_{S1} = \frac{\sum_{t=T_0}^{T_0+RT} A_t \cdot (t - T_0)}{\sum_{t=T_0}^{T_0+RT} A_t}$$

where $A_t$ is the instantaneous value of the accelerometer signal at time t and RT is the time interval between the R-wave and the immediately following T-wave.

19. The device of claim 18, wherein the control circuit comprises a detection circuit that detects when the patient is in a rest condition and wherein the control circuit undertakes adjusting the AV delay through the plurality of AV delay values when the rest condition is detected.

20. The device of claim 18, wherein the monitoring circuit is operative to calculate a maximum peak-to-peak accelerometer signal (S1) that corresponds to a first heart sound occurring within a first pre-defined interval.

21. The device of claim 20, wherein the first pre-defined interval comprises the time from the delivery of a ventricular stimulation pulse to an occurrence of an immediately following T-wave.

22. The device of claim 18, wherein the control circuit is configured to control the pulse generator to deliver a plurality of stimulation pulses at each one of a plurality of AV delay values and to form an average value of the accelerometer signals at each AV delay value.

23. The device of claim method of claim 18 further comprising an ejection interval (EI) as a measure of cardiac contractility and wherein the ejection interval (EI) comprises calculating the EI from the equation EI=$T_{S2}$−$T_{S1}$ where $T_{S2}$ is calculated from the equation:

$$T_{S2} = RT + \frac{\sum_{t=RT}^{nextT_0} A_t^2 \cdot (t - RT)}{\sum_{t=RT}^{nextT_0} A_t^2}$$

where $A_t$ is the instantaneous value of the accelerometer signal at time t and RT is the time interval between the R-wave and the immediately following T-wave and next $T_0$ is R-wave immediately following the T-wave.

* * * * *